United States Patent [19]

Okano et al.

[11] 4,390,028
[45] Jun. 28, 1983

[54] OCCLUSION PRESSURE SENSOR

[75] Inventors: Michiaki Okano, Uji; Shuhei Furuichi, Shiga, both of Japan

[73] Assignee: Kabushiki Kaisha Morita Seisakusho, Kyoto, Japan

[21] Appl. No.: 247,272

[22] Filed: Mar. 25, 1981

[30] Foreign Application Priority Data

Mar. 24, 1980 [JP] Japan .................................. 55-37778

[51] Int. Cl.³ .............................................. A61B 5/10
[52] U.S. Cl. ...................................... 128/777; 433/68
[58] Field of Search ............... 128/777, 774, 776, 779, 128/782, 639, 642; 433/68–71, 214; 340/665–666; 73/65

[56] References Cited

U.S. PATENT DOCUMENTS

| | | | |
|---|---|---|---|
| 1,891,751 | 12/1932 | Coyne | 340/666 X |
| 3,836,900 | 9/1974 | Mansfield | 128/782 X |
| 4,194,194 | 3/1980 | Redfern | 340/665 X |
| 4,250,894 | 2/1981 | Frei et al. | 128/774 |
| 4,287,895 | 9/1981 | Hori | 128/782 X |
| 4,310,002 | 1/1982 | Takinishi et al. | 128/642 |

FOREIGN PATENT DOCUMENTS

| | | | |
|---|---|---|---|
| 2235521 | 1/1974 | Fed. Rep. of Germany | 340/666 |
| 634736 | 11/1978 | U.S.S.R. | 128/782 |

*Primary Examiner*—Lee S. Cohen
*Assistant Examiner*—Angela D. Sykes
*Attorney, Agent, or Firm*—Koda and Androlia

[57] ABSTRACT

The disclosure relates to an occlusion pressure sensor of the construction in which pressure sensitive block changing in electric characteristic under external pressure are arranged in multiple rows. The occlusion pressure sensor is designed to detect an electric signal responsive to occlusion pressure from the pressure sensitive blocks by successively and electrically scanning the blocks in the state of a patient engaging his teeth.

8 Claims, 13 Drawing Figures

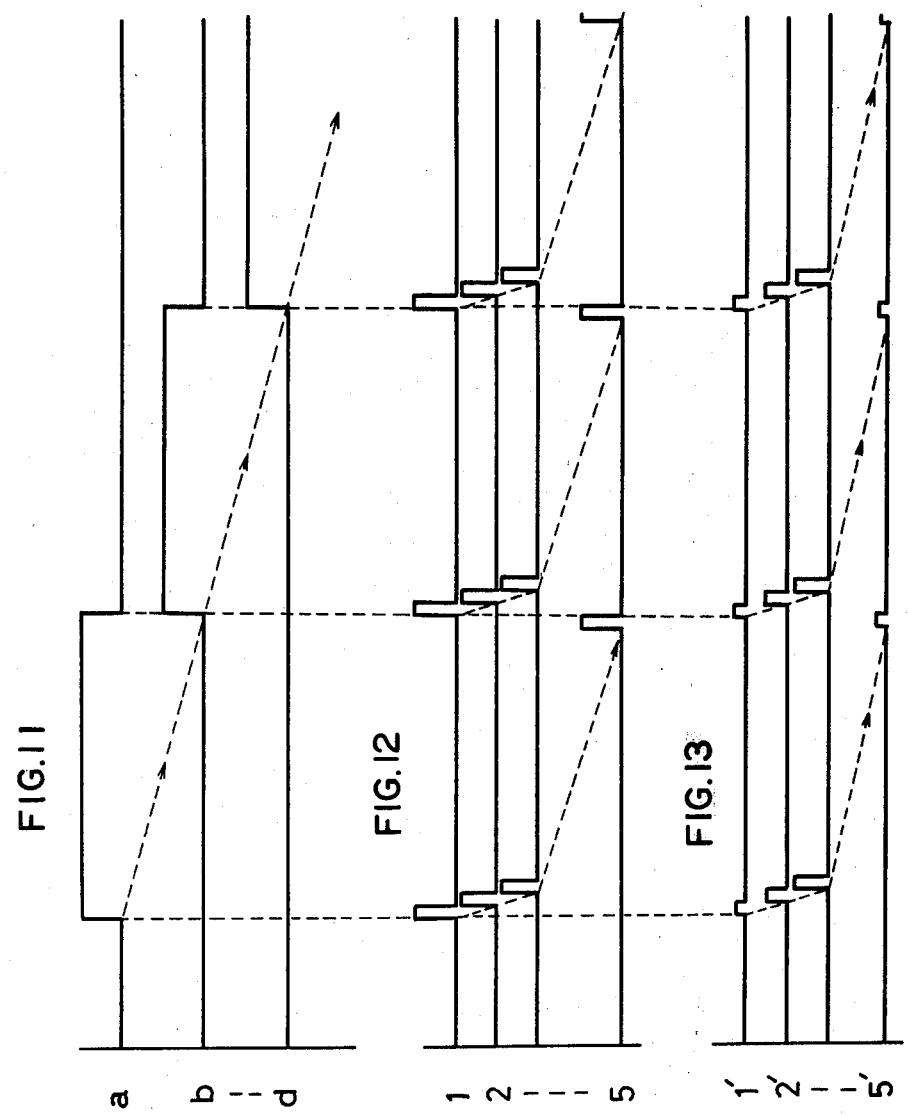

OCCLUSION PRESSURE SENSOR

BACKGROUND OF THE INVENTION

1. Field of the Invention

This invention relates to an occlusion pressure sensor and more particularly to an occlusion pressure sensor detecting occlusion pressure produced at occluding points of the teeth in terms of electric signal.

2. Prior Art

It is unquestionably important that proper adjustment of occlusion be made in dental treatment, and it was the conventional practice to determine whether occlusion is proper by having a patient bite occluding paper, similar to carbon paper in copying, an occluding ribbon, similar to an inked ribbon for typewriter, occluding wax, a thin wax sheet for shaping, and analyzing impressions of the teeth, namely the color transferred onto the occluding points or occluding surface of the teeth and strength of the color patterns of the decolorized portions by transfer of color onto the teeth, state of depression, etc.

Although the method described above provides information on general occlusion pressure, it cannot provide the exact distribution of strength of occlusion pressure and can provide only the results of occlusion carried out once or of accumulation of occlusion effected several times. Accordingly, it was impossible to realize the progress of occlusion in terms of time from the state of the teeth beginning to make contact with each other to the state of strong occlusion. The knowledge of such progress of occlusion is also necessary for the examination of the initial contact considered important at the time of adjustment of dental occlusion. In addition thereto, it is no less necessary to analyze not only upper occlusion and lower occlusion, but also right and left and backward and forward slide at the time of adjustment of dental occlusion. Nevertheless, it was impossible in principle to examine such occlusion and slide simultaneously by the conventional practice using occluding paper, occluding ribbon and occluding wax.

SUMMARY OF THE INVENTION

Accordingly, it is an object of this invention to provide a pressure sensitive sensor capable of obtaining information on occlusion pressure produced at various points of occlusion in terms of an electric signal by a patient engaging the upper with the lower teeth simply in the mouth.

It is a further object of the invention to provide a pressure sensitive sensor capable of providing a dentist with information on occlusion pressure produced at occluding points at real time in the state of a patient engaging the upper with the lower teeth in the mouth.

It is still another object of the invention to provide a pressure sensitive sensor capable of providing information on changes in occlusion pressure in the course of time from the time that the teeth begin to make contact with each other to the time at which the teeth are brought into the state of strong occlusion.

In the achievement of these objects, there is provided a pressure sensor for detecting occlusion pressure which comprises a complex pressure sensitive element consisting of a rectifying layer and a pressure sensitive layer, the element changing electric characteristic thereof in response to occlusion pressure by catching the occlusion pressure of the teeth an upside electrode and an underside electrode, the electrodes being constructed by arranging thin strip pieces or segments in such manner that the strip pieces or segments are arranged on the upper and lower surfaces of the element in regularly crossing or coordinated relation vertical of the complex pressure sensitive element so as to form a plurality of pressure sensitive blocks marked off from one another in the pressure sensitive element, and an insulating film, the film including the upside and underside electrodes and encircling and covering the complex pressure sensitive element.

BRIEF DESCRIPTION OF THE DRAWINGS

FIGS. 11, 12 and 13 respectively show timing charts of a rank-scanning pulse, a file-scanning pulse and an output pulse signal of the invention.

DETAILED DESCRIPTION OF THE INVENTION

A detailed description will now be given of embodiments of the sensor of the invention with reference to the accompanying drawings.

Figure 1:
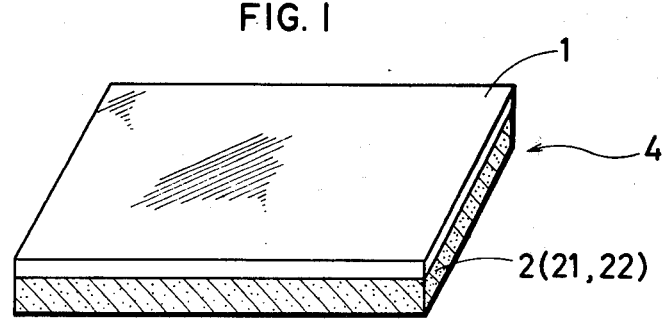
FIG. 1 is a perspective view showing an embodiment of a pressure sensitive element of this invention.
Figure 2:
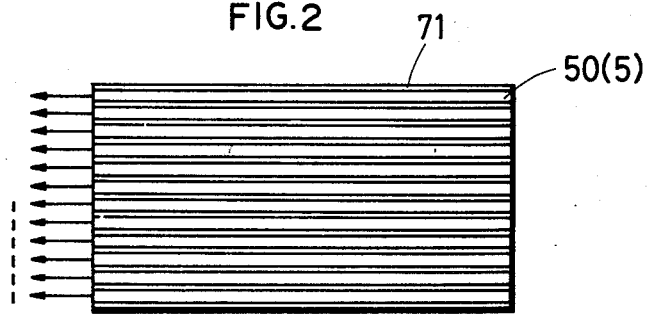
FIGS. 2 and 3 respectively show an arrangement of an upside electrode and an underside electrode.
Figure 3:
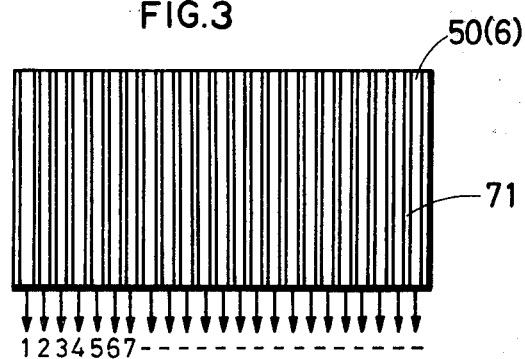
Figure 10:
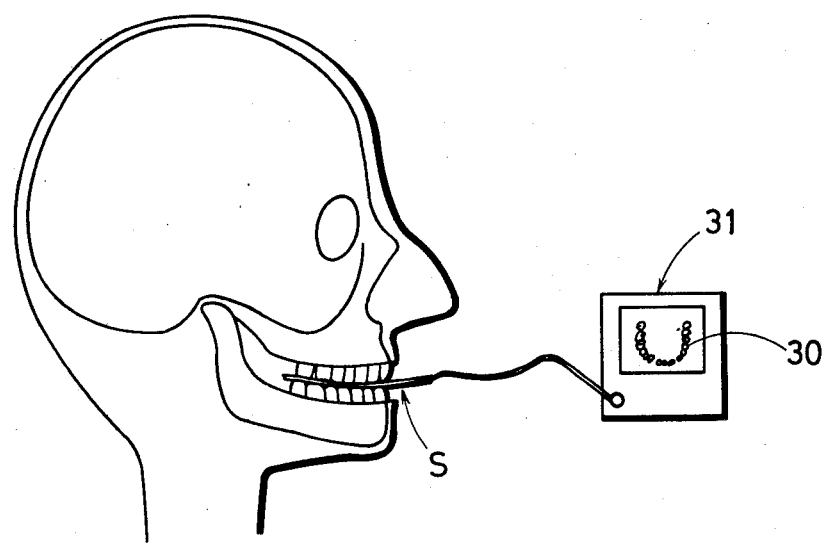
FIG. 10 shows how the invention is used with a patient in dental treatment.

FIG. 1 shows a thin plate-like complex pressure sensitive element 4 constructed of a pressure sensitive layer 2 laminated over the underside of a rectifying layer 1, which pressure sensitive layer 2 changes electric characteristic thereof by being subjected to external pressure. FIGS. 2 and 3 respectively show an arrangement of an upside and underside electrodes constructed in multiple row arrangement wherein longitudinal strip electrodes 50 . . . are provided in side-by-side relation spaced by insulating materials 71 . . . from one another. The reference characters a, b, c, d, . . . and 1, 2, 3, 4 . . . designated leading-in wires conducted from the strip electrodes 50 . . . . The leading-in wires, as shown in FIG. 10, are housed in one flat insulating tube, conducted out of an occlusion pressure sensor and adapted to conduct occlusion pressure signals in the form of electric signals generated by the occlusion pressure sensor to outside.

Figure 4:
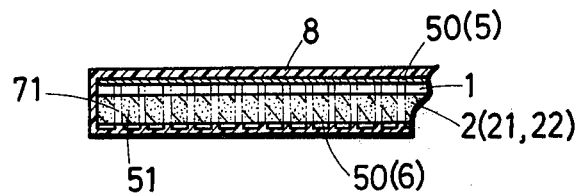
FIG. 4 is a longitudinal sectional view, broken in part, of the occlusion pressure sensor.

According to the occlusion pressure sensor shown in the embodiment, the strip electrodes 50 . . . (5) are arranged and constructed on the upside of the complex pressure sensitive element 4 of the construction shown in FIG. 1, and strip electrodes 50 . . . (6) are arranged and constructed on the underside of the element 4 as shown in FIG. 3 so as to sandwhich the element between the electrodes (5) and (6) in the manner that the strip electrodes 50 . . . on the upside and the underside of the element are arranged and constructed in mutually three-dimensionally intersecting relation. Pressure sensitive blocks 51 . . . are constructed in three dimensionally duplicate portion of the strip electrodes 50 ... on the upside of element 4 and the strip electrodes on the underside thereof with the element 4 sandwiched therebetween. The numeral 8 designates insulation covering that encircles and envelopes the pressure sensitive element 4. FIG. 4 is a longitudinal sectional view, broken in part, of the occlusion pressure sensor.

Figure 5:
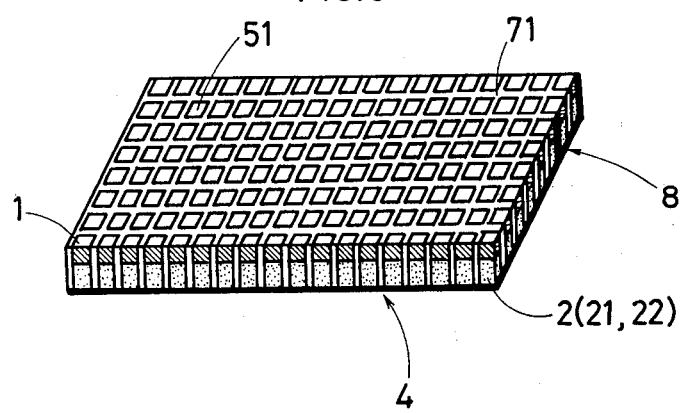
FIG. 5 is a perspective view showing another embodiment of pressure sensitive element.

FIG. 5 is a perspective view of another embodiment of the pressure sensitive element. The pressure sensitive blocks 51 according to this embodiment are constructed by both marking off a complex pressure sensitive element of the construction shown in FIG. 1 in lattice form by insulating members 71 ... and by assembling a plurality of segment electrodes 50 ... in regularly coordinated relation to both on the upside and on the underside of the thus marked-off portions.

Figure 6:
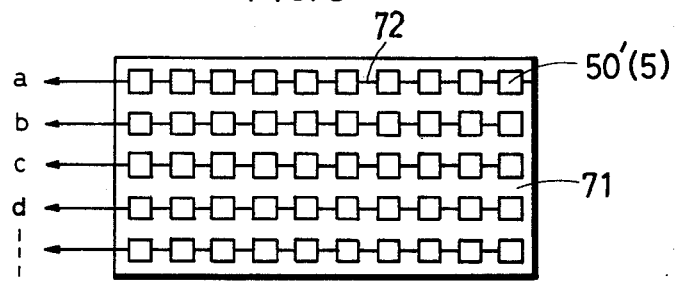
FIGS. 6 and 7 respectively show another embodiment of an upside electrode and an underside electrode.
Figure 7:
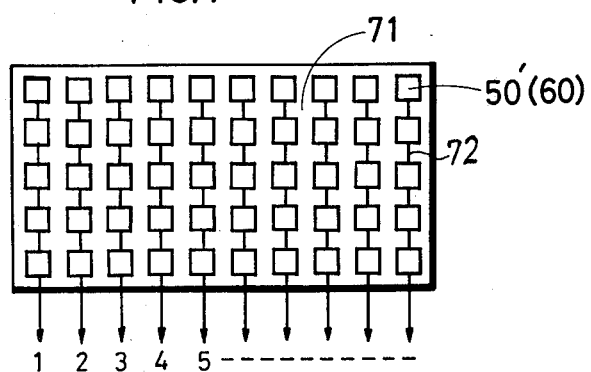

FIGS. 6 and 7 respectively show the arrangement of the upside and underside electrodes arranged on the upside and underside of the complex pressure sensitive element 4 shown in FIG. 4. In the figures, strip electrodes 50' ... arranged on the upside and underside of the element 4 are respectively connected in series by thin conductors 72 ... in each file or in each rank arrangement.

Figure 8:
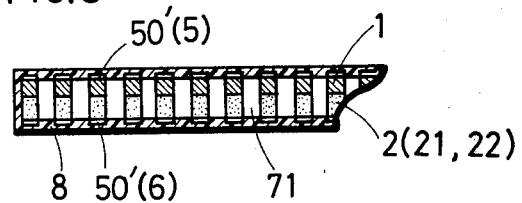
FIG. 8 is a longitudinal sectional view, broken in part, of another embodiment of the invention.

FIG. 8 is a longitudinal sectional view, broken in part, of an occlusion pressure sensor wherein the numeral 8 designates an insulating film encircling and covering the complex pressure sensitive element 4 constructed as above.

In the two embodiments illustrated, so long as the rectifying layer 1 has the property of permitting the flow of current in one direction but preventing that of current in the opposite direction, the layer 1, irrespective of whatever material may form the layer, can be selected from all kinds of material or complex such as a selenium rectifying material of Se layer and a complex laminated material Fe consisting both of OdS layer and $Ou_2S$ layer, a selenium rectifying material Al layer and Se layer, a cuprous oxide rectifying material comprising Cu layer and $Cu_2O$ layer, a Schottky rectifying material having a film as of Au, Ni, W, Mo, V formed on the surface Si, Ge or GaAs layer and a semiconductor formed by P-N junction of Si or Ge semiconductor. A material usable as a pressure sensitive layer 2 may be the one 21 (such as vinylidene polyfluoride film (PVDF film), zirconium titanate film (PZT film)) or may be the one 22 that changes the electric resistance thereof in response to the external pressure applied (for example all materials such as pressure sensitive rubber possessed with pressure sensitivity by mixing metal or carbon particles into rubber, a film having a pressure resistant effect and in which a semiconductor such as Si is used, a cell containing carbon particles) and other complexes may suitably be selected so long as they change the electric characteristic thereof under external pressure, no matter whatever material they may be. On the other hand, the upside electrode 5 and the underside electrode 6 may be formed by directly vapor coating and metalizing an electroconductive metal as of aluminum and silver at suitable points on the respective sides of the pressure sensitive element 4 or may be formed separately by vapor coating or metalizing an electroconductive material such as aluminum and silver on an insulating substrate such as of ceramic and synthetic resin. In short, recourse may be had to any other means that is sufficient to constitute pressure sensitive blocks 51 ... containing pressure sensitive element 4 and marked off in lattice form.

Figure 9:
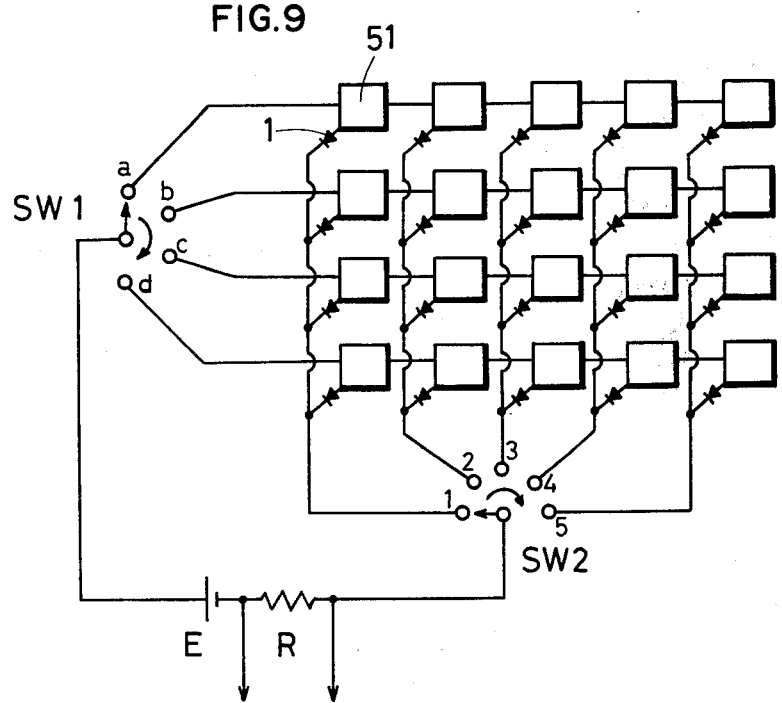
FIG. 9 shows an electrically equivalent circuit of the invention.

FIG. 9 is an equivalent typical electric circuit diagram showing electrical structure of the sensor of the invention, wherein the numerals 51 ... designate pressure sensitive blocks and 1 designates diodes which show equivalently a rectifying layer.

The structure of the sensor of the invention is electrically shown as a diode matrix of the type described above. The reference character SW1 designates a switching mechanism for energizing and scanning the upside electrode 5 of the sensor constructed of strip or segment electrodes 50 ... and 51' ... and SW2 designates a switching mechanism for energizing and scanning the underside electrode 6 of the sensor constructed of strip or segment electrodes 50 ... and 5' ..., and E designates a DC power source used when a change in the electric characteristic of the pressure sensitive blocks 51 ... represents a resistance change, and the source is considered unnecessary when a change in the electric characteristic of the pressure sensitive blocks 51 ... represents a resistance change.

A description will now be given of the use of the sensor of the invention and of the operating principle thereof with reference to the drawings. A user bites a sensor S by the upper and lower teeth in the mouth as shown in FIG. 10. In this state, all that is necessary to do is to electrically and scan all the pressure sensitive blocks 51 ... and derive an electric signal responsive to occlusion pressure from the blocks 51 ....

This derivation of electric signal is effected by switching switches SW1 and SW2, and this switching operation may readily be made by use of an electronic switch. More specifically, during the time that the electrodes connected in each rank out of the upside electrode 5 are energized by switching operation of SW1 (to be referred hereinafter as rank-scanning), the electrodes connected in each rank out of the underside electrode 6 are energized successively (to be referred to hereinafter as file-scanning). By so doing, the pressure sensitive blocks 51 ... arranged in lattice form are successively scanned and a change in electric characteristic effected by occlusion pressure is electrically converted into an electric signal output. FIGS. 11 and 12 respectively show time charts both for rank-scanning pulse and for file-scanning pulse in scanning of the kind described above. FIG. 13 is a diagram illustrating the occlusion pressure signal (pulse) outputted from the pressure sensitive blocks. In FIG. 9, the electric signal if converted into voltage and is conducted outside through a resistor R. Switching of switches from SW1 to SW2 is successively operated in synchronism with the horizontal and vertical scanning of CRT 30 provided in housing 31 to thereby lead the output signal of occlusion sensor S to a brilliance modulation circuit and indication of the output signal of CRT picture provides a picture of an occlusion pressure change in the teeth panoramically and at real time.

In addition, the invention may be used in combination with a video tape recording device or graphic display equipment. It should be understood that combined use of other suitable devices makes it possible to provide information on occlusion pressure not only in the form of a moving image but also in the form of a still image.

As described above, since the invention makes it possible to correctly detect an electric signal responsive to occlusion pressure in each pressure sensitive block, the invention is of great use to dental treatment in that it enables the operator to grasp the occlusion pressure distribution over the entire jaws more positively and at real time.

We claim:

1. A sensor for occlusion pressure comprising:
   a complex pressure sensitive element including a rectifying layer and a pressure sensitive layer;
   said element changing electric characteristic thereof in response to occlusion pressure by detecting the occlusion pressure of the teeth;
   an upside electrode and an underside electrode;
   said electrodes being constructed by arranging thin strip pieces or segments in such manner that said strip pieces or segments are arranged in regularly crossing or coordinated relation vertically of said pressure sensitive element on the upside and underside of the element so as to form a plurality of pressure sensitive blocks marked off from one another on the pressure sensitive element; and
   an insulating film, said film surrounding and covering said upside and underside electrodes and said complex pressure sensitive element;
   whereby said sensor is constructed to detect an electric signal responsive to occluding points and occlusion pressure from said pressure sensitive blocks by successively electrically scanning the blocks.

2. A sensor according to claim 1, wherein said complex pressure sensitive element comprises a piezoelectric layer laminated over the underside of a rectifying layer.

3. A sensor according to claim 1, wherein said complex pressure sensitive element comprises a pressure sensitive resistant layer laminated over the underside of a rectifying layer.

4. A sensor according to claim 2, wherein said piezoelectric layer is formed of a piezoelectric thin film.

5. A sensor according to claim 3, wherein said pressure sensitive resistant layer is formed of pressure sensitive rubber.

6. A sensor according to claim 2 or 3, wherein said rectifying layer is formed of a selenium rectifying material.

7. A sensor according to claim 2 or 3, wherein said rectifying layer is formed of a Schottky rectifying material.

8. A sensor according to any of claims 1 to 5, wherein said pressure sensitive blocks are formed in regular shapes and arranged continuously in lattice form.

* * * * *